United States Patent [19]

Thornton

[11] 4,217,099
[45] Aug. 12, 1980

[54] DEVICE FOR INSERTING ELASTOMERIC SEPARATION RINGS BETWEEN TEETH

[76] Inventor: Charles B. Thornton, 4555 Whisper Lake Dr. No. 2, Florissant, Mo. 63033

[21] Appl. No.: 28,245

[22] Filed: Apr. 9, 1979

[51] Int. Cl.² ............................................. A61C 7/00
[52] U.S. Cl. ...................................... 433/148; 433/18
[58] Field of Search ......................... 433/18, 11, 148; 221/33; 206/805

[56] References Cited

U.S. PATENT DOCUMENTS

| | | | |
|---|---|---|---|
| 2,328,522 | 8/1943 | Yocum | 221/33 |
| 4,038,753 | 8/1977 | Klein | 433/18 |

OTHER PUBLICATIONS

"The Elastomeric Separator: A Simple Method to Gain Space," New Zealand Dental Journal, vol. 74, Jan. 78, pp. 33-35, CPJ. McClez.

*Primary Examiner*—Robert Peshock
*Attorney, Agent, or Firm*—Senniger, Powers, Leavitt and Roedel

[57] ABSTRACT

A device for inserting an elastomeric separation ring between adjacent teeth in a person's mouth, comprising a ring holder comprising a stem adapted to extend through and to hold a series of rings, a closed loop of strand material extending from one end of the ring holder and being adapted to receive rings thereon so that two segments of the loop pass through the opening in the ring, and two stops for the rings one stop at each end of the ring holder. In the use of the device when a series of rings is held on the ring holder, one of the rings on the stem is moved onto the loop of strand material, the loop of strand material is formed into two loops one on each side of the ring, the two loops are elongated in a direction radially of the ring so as to deform the ring into a narrower thickness, the deformed ring is inserted between adjacent teeth and thereafter the loop of strand material is pulled through the ring to remove the loop of strand material from the person's mouth, thereby allowing the elastic forces in the ring to return it toward its undeformed shape, to thus cause the teeth to be moved apart to increase the spacing therebetween.

7 Claims, 6 Drawing Figures

U.S. Patent    Aug. 12, 1980    4,217,099
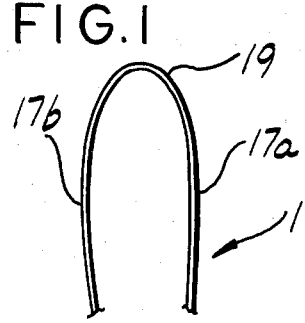
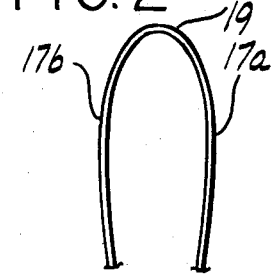
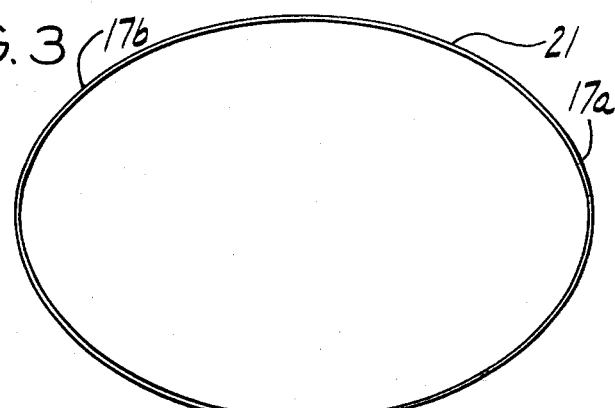
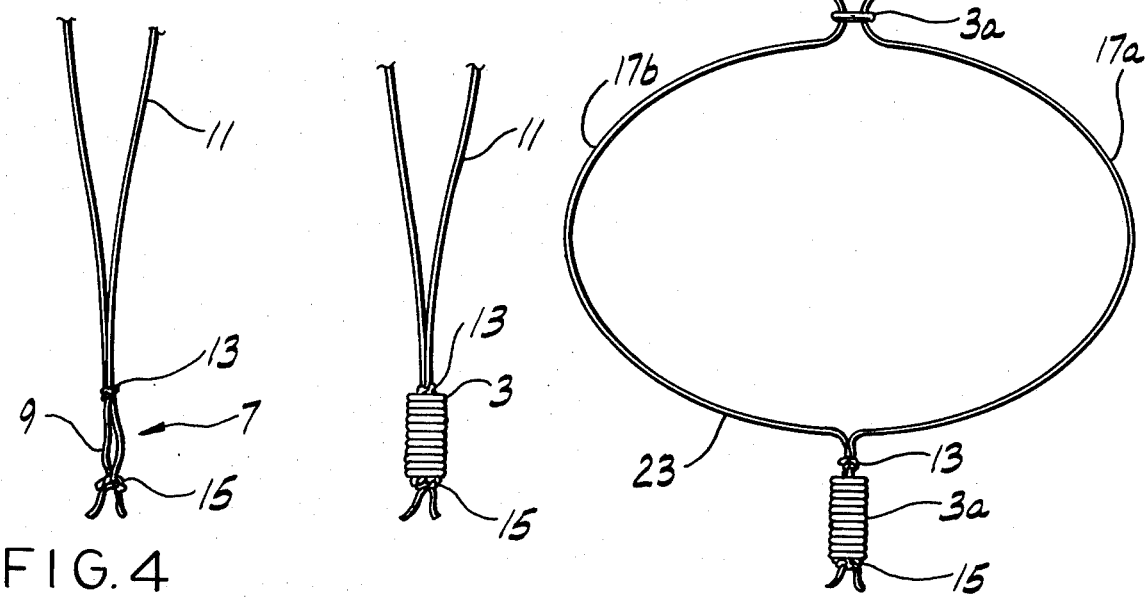
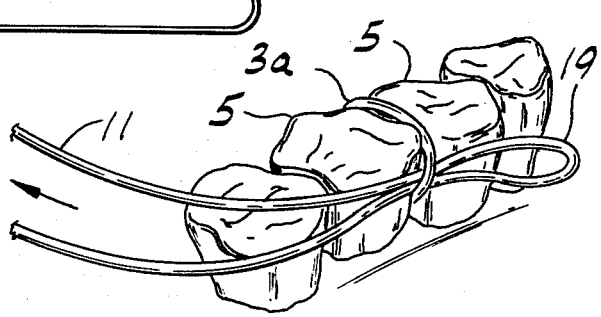
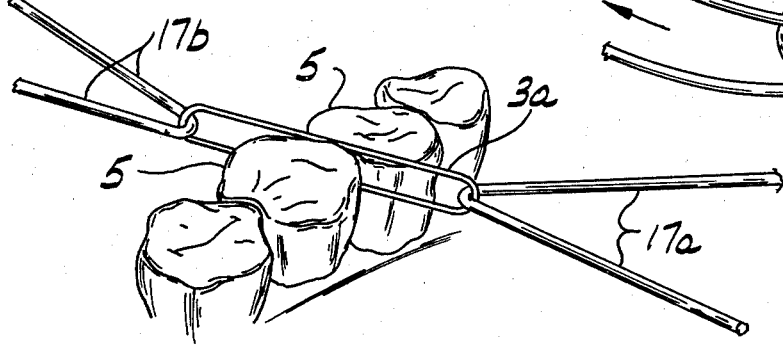

DEVICE FOR INSERTING ELASTOMERIC SEPARATION RINGS BETWEEN TEETH

BACKGROUND OF THE INVENTION

This invention relates to elastomeric rings used to separate adjacent teeth in a person's mouth, and more particularly to a device for installing such rings between the teeth and a method for utilizing the device to install the rings.

Elastomeric rings have been used by orthodontists to separate adjacent teeth in a patient's mouth to the required spacing prior to fitting orthadontic bands on the teeth. To permit insertion of a ring between the teeth, the ring is stretched radially to effect elastic deformation of the ring into a narrower thickness (i.e., a thickness approximately the then existing distance between the teeth). Once the ring is inserted the radial stress on the ring is removed, but the ring remains deformed elastically by the constrictive force of the teeth between which it is disposed. Over time, the elastic forces in the ring tending to return it to its original (i.e., undeformed) thickness cause the teeth to be moved apart to increase the spacing therebetween. Due to the small size of the rings (approximately 0.15 inch outer diameter and 0.05 inch inner diameter), handling of the rings has proven to be difficult and the process of inserting the rings time consuming.

SUMMARY OF THE INVENTION

Among the several objects of this invention may be noted the provision of a device for easily and rapidly inserting elastomeric rings between adjacent teeth in a person's mouth; the provision of such a device which holds a series of elastomeric rings to be inserted; the provision of such a device which can be used both by orthodontists and patients; the provision of such a device which can be reused, the provision of such device which is so inexpensive as to be disposable; and the provision of a method of utilizing the device.

Briefly, the device of this invention comprises a ring holder comprising a stem adapted to extend through and to hold a series of rings, a closed loop of strand material extending from one end of said stem and adapted to receive rings from said ring holder thereon so that two segments of the loop pass through the opening in the ring, and first and second stops for the rings. The first stop is at said one end of the stem and has a lateral dimension slightly larger than that of the opening in each of the rings, so that the first stop may impede but not completely block movement of the rings therepast. The second stop is at the other end of the stem and has a lateral dimension substantially larger than that of the opening in each of the rings, so that the second stop may completely block movement of the rings therepast. With one of the rings received on the loop of strand material, the loop of strand material may be formed into two loops one on each side of the ring and, when these loops are pulled in a direction radially of the ring, the ring may be stretched to effect elastic deformation of the ring to a narrower thickness facilitating the insertion of the ring between adjacent teeth in a person's mouth. Briefly, the method of utilizing the device, when a series of rings is held on the stem of the ring holder comprises, moving one of the rings from the ring holder onto the loop of strand material, forming the loop of strand material into two loops one on each side of the ring, elongating the two loops in a direction radially of the ring to deform the ring into a narrower thickness, inserting the deformed ring between adjacent teeth, and pulling the loop of strand material through the inserted ring to remove the device from the patient's mouth and to allow the ring to return toward its original thickness, thereby moving the teeth apart.

Other objects and features will be in part apparent and in part pointed out hereinafter.

BRIEF DESCRIPTION OF THE DRAWINGS

FIG. 1 is an elevation of the device of this invention with a portion of its length broken away;

FIG. 2 is a view similar to FIG. 1 showing a series of rings on the ring holder;

FIG. 3 is an elevation showing one ring moved onto the loop of string material;

FIG. 4 is a view similar to FIG. 3 showing the loop formed into two elongated loops and the ring deformed into a narrower thickness;

FIG. 5 is an enlarged perspective of the deformed ring during its insertion between adjacent teeth; and FIG. 6 is a view similar to FIG. 5 showing the device partially removed from the inserted ring.

Corresponding reference characters indicate corresponding parts throughout the several views of the drawings.

DESCRIPTION OF THE PREFERRED EMBODIMENT

Referring to the drawings, there is generally indicated at 1 a device of this invention for inserting elastomeric rings 3 between adjacent teeth 5 in a person's mouth, comprising a ring holder 7 comprising means forming a stem 9 adapted to extend through and to hold a series of rings 3, a closed loop 11 of strand material extending from one end of the stem 9, a first stop 13 for the rings 3 at said one end of the stem, and a second stop 15 for the rings at the other end of the stem.

Preferably, the ring holder 7 comprises a length of strand material, such as waxed or plastic string-like material (i.e. dental floss). Alternatively, the ring holder 7 may comprise a length of solid material, such as a rod or bar of plastic material. The material of the ring holder, whether strand or solid, forms a stem 9 having lateral dimensions less than that of the opening in each of the rings 3, so that the rings may readily slide over the stem. The stem 9 is long enough (e.g., ½ to 1 inch) to hold a series of the rings thereon.

The loop 11 of strand material extends from one end of the stem 9 and is adapted to receive rings 3 thereon so that two segments of the strand pass through the opening of the ring. This strand material, like that of the stem, may be waxed or plastic string-like material (i.e. dental floss). The loop comprises two reaches 17a and 17b each of a different color. When the reaches 17a and 17b are in engagement or closely adjacent along their length, the lateral dimensions of the loop 11 of strand material are less than that of the opening in each ring, so that the rings 3 may be received onto the loop 11 from the ring holder 7 or at a looped end 19 of the loop 11 and moved along the length of the loop 11. When elongated in a direction parallel to the stem, the loop 11 of strand material is 12 to 18 inches long (i.e., the distance from the ring holder 7 to the looped end 17). This length facilitates the handling of the device by the user, as explained hereinafter.

The first stop 13 for the rings has a lateral dimension slightly larger than that of the opening in each of the rings 3, so that it may impede but not completely block movement of the rings therepast. The second stop 15 for the rings has a lateral dimension substantially larger than the opening in each of the rings, so that it completely blocks movement of the rings therepast. The first and second stops preferably comprise knots tied in the stem 9 at the ends thereof. Thus, the device 1 may be formed of a single continuous length of strand material looped and tied with two knots toward the free ends of the material. Alternatively, the first and second stops may be separate elements secured onto the stem.

In the method of utilizing the device 1 to insert rings between adjacent teeth 5 in a person's mouth, a series of rings are placed on stem 9 of the ring holder 7 (see FIG. 2). The rings can be positioned on the ring holder by sliding them over the loop 11 of the string material at its looped end 19, moving them along the loop 11 toward the stem 9, and forcing them past the first stop 13 onto the stem 9.

With the series of rings 3 on the ring holder 7, a single ring 3a is forced past the first stop 13 and moved along the loop 11 to a point approximately midway between its looped end 19 and the first stop 13. Two smaller loops 21 and 23 are then formed in the device 1, one on each side of the ring 3a (see FIG. 3).

The two loops 21 and 23 are pulled in a direction radially of the ring 3a (see FIGS. 3 and 4) to deform the ring into a narrower thickness. To deform the ring 3a when pulling the loops 21 and 23, it is essential that each of these loops pass through the ring (see FIG. 3). If loop 11 of strand material were formed in a figure "8" pattern with the ring disposed at the point where the segments of the loop cross, elongation of the loops would not cause the ring to deform. Coloring the two reaches 17a and 17b of the loop differently helps the user form the proper loops. The user merely grasps the loop ends of one color in one hand and the loop ends of the other color in the other hand and moves his hands apart to pull the loops and deform the ring 3a.

With the ring 3a deformed to a narrower thickness, the ring is inserted between adjacent teeth 5 in a person's mouth (see FIG. 5). If space already exists between the teeth, ring 3a can be deformed sufficiently thin to merely move the ring 3a into this space. However, when the teeth are in engagement, it may be necessary also to use a sawing action to move the ring 3a between the teeth. The earlier mentioned length of the loop 11 of strand material enables the user to grasp and hold the loops 21 and 23 in his hands without using his index fingers, thereby enabling the user to guide the ring 3a between the teeth with his index fingers.

With the ring 3a inserted in his teeth, the device 1 is removed from the person's mouth by pulling the ring holder 7 away from the ring 3a, thus drawing the loop 11 of strand material through the opening in the ring 3a (see FIG. 6). The ring 3a is then deformed only by the constrictive force of the teeth between which it is disposed. Over time, the elastic force of the ring which tends to return it to its original thickness causes the teeth to be moved apart to increase the space therebetween.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limited sense.

What is claimed is:

1. A device for inserting an elastomeric separation ring between adjacent teeth in a person's mouth, comprising:
    a ring holder comprising a stem adapted to extend through and to hold a series of rings;
    a series of rings on said stem;
    a closed loop of strand material extending from one end of said stem and adapted to receive a ring thereon so that two segments of the closed loop pass through the opening in the ring;
    a first stop for the rings at said one end of the stem, having a lateral dimension slightly larger than that of the opening in each of the rings, so that said first stop may impede but not completely block movement of the rings therepast; and
    a second stop for the rings at the other end of the stem, having a lateral dimension substantially larger than the opening in each of the rings so that said second stop may completely block movement of the rings therepast;
    whereby when a ring is received on said loop of strand material, said closed loop of strand material may be formed into two smaller loops one on each side of said ring, which when pulled in a direction radially of the ring stretch said ring to effect elastic deformation thereof to a narrower thickness facilitating the insertion of the ring between adjacent teeth in the patient's mouth.

2. A device as set forth in claim 1 wherein said stem comprises a length of strand material.

3. A device as set forth in claim 2 wherein said stops comprise knots tied in said stem at the ends thereof.

4. A device as set forth in claim 3 wherein said closed loop of strand material and said stem are formed from a single, continuous length of strand material.

5. A device as set forth in claim 1 wherein said reaches are of a different color to facilitate forming said closed loop of strand material into said two loops.

6. The method for inserting an elastomeric ring between adjacent teeth in a person's mouth utilizing a device comprising a ring holder comprising means forming a stem extending through and holding a series of rings, a closed loop of strand material extending from one end of said stem, said closed loop being adapted to receive a ring thereon, a first stop for the rings at said one end of the stem and a second stop for the rings at the other end of the stem; said method comprising:
    moving one of the rings from the ring holder onto the closed loop of strand material;
    forming the closed loop of strand material into two loops one on each side of said one ring;
    elongating said two loops in a direction radially of the ring so as to deform said ring into a narrower thickness;
    inserting said ring, when deformed, between adjacent teeth in a person's mouth, and
    thereafter pulling the closed loop of strand material through said one ring to remove the device from the person's mouth and to allow said one ring to return toward its undeformed shape.

7. The method of claim 6 wherein said rings are placed on said ring holder by passing a plurality of rings on said closed loop of strand material at a looped end remote from said ring holder, moving said plurality of rings toward said ring holder along said closed loop of strand material, and forcing said plurality of rings past said first stop onto the stem of the ring holder, said plurality of rings moved onto the ring holder constituting at least a portion of said series of rings held on the stem of the ring holder.

* * * * *